United States Patent
Treacy et al.

(10) Patent No.: US 10,004,617 B2
(45) Date of Patent: Jun. 26, 2018

(54) WOVEN STENT DEVICE AND MANUFACTURING METHOD

(71) Applicant: COOK MEDICAL TECHNOLOGIES LLC, Bloomington, IN (US)

(72) Inventors: Gerard Thomas Treacy, Limerick (IE); Don Frawley, Limerick (IE); John Neilan, Galway (IE)

(73) Assignee: Cook Medical Technologies LLC, Bloomington, IN (US)

( * ) Notice: Subject to any disclaimer, the term of this patent is extended or adjusted under 35 U.S.C. 154(b) by 1 day.

(21) Appl. No.: 14/887,950

(22) Filed: Oct. 20, 2015

(65) Prior Publication Data

US 2017/0105854 A1 Apr. 20, 2017

(51) Int. Cl.
*A61F 2/88* (2006.01)
*A61F 2/90* (2013.01)

(52) U.S. Cl.
CPC ............... *A61F 2/88* (2013.01); *A61F 2/90* (2013.01); *A61F 2220/0075* (2013.01); *A61F 2240/001* (2013.01); *A61F 2250/0098* (2013.01)

(58) Field of Classification Search
None
See application file for complete search history.

(56) References Cited

U.S. PATENT DOCUMENTS

| | | |
|---|---|---|
| 1,945,195 A | 1/1934 | Kellems |
| 6,162,244 A | 12/2000 | Braun et al. |
| 6,280,467 B1 | 8/2001 | Leonhardt |
| 6,468,301 B1 | 10/2002 | Amplatz et al. |
| 6,558,418 B2 | 5/2003 | Carpentier et al. |
| 6,632,241 B1 | 10/2003 | Hancock et al. |
| 6,656,218 B1 | 12/2003 | Denardo et al. |
| 6,786,919 B1 | 9/2004 | Escano et al. |
| 7,329,279 B2 | 2/2008 | Haug et al. |
| 7,402,170 B2 | 7/2008 | McCullagh et al. |
| 7,462,190 B2 | 12/2008 | Lombardi |
| 7,462,192 B2 | 12/2008 | Norton et al. |
| 7,655,039 B2 | 2/2010 | Leanna et al. |

(Continued)

FOREIGN PATENT DOCUMENTS

| | | |
|---|---|---|
| WO | WO 2006/124541 A1 | 11/2006 |
| WO | WO 2008/130530 A1 | 10/2008 |
| WO | 2012/110355 A1 | 8/2012 |

OTHER PUBLICATIONS

European Search Report for EP 16194189 dated Feb. 16, 2017 in related application.

*Primary Examiner* — Thomas J Sweet
*Assistant Examiner* — Megan Wolf
(74) *Attorney, Agent, or Firm* — Brinks Gilson & Lione

(57) ABSTRACT

A stent and method for treating an end of a pre-woven stent is provided. The method includes providing a pre-woven stent including a plurality of sharp ends. A pair of wire portions that extend in opposite helical directions around the stent are bent and woven into the stent to define a pair of overlapping crown portions. When the wires are woven into the stent a double weave portion of the stent is defined. The wires can be cut to define tail portions that are removed from the stent, leaving a single crown portion. The sharp ends can be alternatively treated by curving the ends to define rounded looped ends.

15 Claims, 4 Drawing Sheets

(56) References Cited

U.S. PATENT DOCUMENTS

| | | |
|---|---|---|
| 7,695,506 B2 | 4/2010 | Thistle et al. |
| 7,993,387 B2 | 8/2011 | Clerc et al. |
| 8,151,682 B2 | 4/2012 | Lilburn et al. |
| 8,353,947 B2 | 1/2013 | Thistle et al. |
| 8,409,270 B2 | 4/2013 | Clerc et al. |
| 8,597,366 B2 | 12/2013 | Shank |
| 8,668,729 B2 | 3/2014 | Kaufmann et al. |
| 8,739,382 B2 | 6/2014 | Sheldon et al. |
| 8,778,011 B2 | 7/2014 | Ryan |
| 2004/0039435 A1 | 2/2004 | Hancock et al. |
| 2004/0186549 A1 | 9/2004 | Jayaraman |
| 2005/0080480 A1 | 4/2005 | Bolea et al. |
| 2008/0290076 A1* | 11/2008 | Sheldon ............ A61F 2/90 219/121.64 |
| 2009/0157158 A1 | 6/2009 | Ondracek et al. |
| 2009/0177268 A1 | 7/2009 | Lundkvist et al. |
| 2011/0265908 A1 | 11/2011 | Clerc et al. |
| 2013/0211492 A1 | 8/2013 | Schneider et al. |
| 2013/0245745 A1 | 9/2013 | Vong et al. |
| 2014/0277371 A1 | 9/2014 | Ryan et al. |
| 2015/0045874 A1 | 2/2015 | McMahon et al. |
| 2015/0045875 A1 | 2/2015 | Hingston et al. |
| 2015/0081000 A1 | 3/2015 | Hossainy et al. |
| 2016/0151180 A1 | 6/2016 | Yokoi et al. |
| 2017/0079812 A1 | 3/2017 | Lam et al. |

* cited by examiner

WOVEN STENT DEVICE AND MANUFACTURING METHOD

TECHNICAL FIELD

The present disclosure relates generally to medical devices, and more particularly to stents having soft crowns.

BACKGROUND

Stents are medical devices commonly used to maintain patency of diseased body vessels, such as those of the vascular and gastrointestinal systems. Stents are often delivered via a minimally invasive procedure and thereafter expanded to contact and support the inner wall of the targeted vessel. In general, most stents include a tubular shaped support structure having a plurality of interstices configured to facilitate compression and expansion of the stent.

Many stents define the tubular shaped structure by weaving a plurality of strands together in a traditional weave pattern, where the strands overlap each other in an alternating fashion, with two major weaving directions. The weaving directions are ultimately in a helical shape, with a first set of strands extending around the stent in the first helical direction, and a second set of strands extending around the stent in a second helical direction that is transverse to the first helical direction.

Many stents define a proximal and distal end of the woven tubular structure, where the ends of the strands terminate to define the proximal and distal ends. The strands are typically in the form of individual wire, so the terminal ends are generally sharp at the proximal and distal ends.

In many instances, the stents include proximal and distal flanges or flared ends to prevent stent migration subsequent to implantation. Flanges or flares are typically set to a larger expanded diameter relative to the stent central portion and may exert a higher radial force per unit area against the vessel wall, thereby securing the stent in position. One problem with these features, however, is that the flanges or flares can damage the vessel wall if they are excessively rigid, especially in light of the sharp ends of the strands. The resulting tissue perforations may be painful and can lead to more serious complications including infection, hemorrhage, and possibly death.

Accordingly, there have been attempts to "treat" the sharp ends of woven stents to reduce the effects of the sharpness of the terminal ends. One method of treating the sharp ends of the woven stent includes welding or soldering a curved member to the sharp ends to join a pair of sharps ends to create a weld joint. However, fatigue stresses become concentrated at the weld joint, which can lead to breaking and exposing of a sharp end, which can lead to injury to the patient.

SUMMARY

The present disclosure generally provides a stent with treated ends and a method for treating the ends of a stent.

Accordingly, in one aspect, a method for treating one or more ends of a pre-woven stent to manufacture a stent comprises the steps of: providing a pre-woven stent defining a body having a tubular body portion, a first end portion, and a second end portion defined by a plurality of wires extending in a first helical direction around the body and extending in a second helical direction around the body, the first helical direction being transverse to the second helical direction, wherein the plurality of wires define a plurality of wire ends terminating at the first end portion, wherein the plurality of wires are woven together to define a plurality of cells and a plurality of intersections; bending a first loose wire portion of the plurality of wires around a bend point to define a first crown portion, and weaving the first loose wire portion into the body of the pre-woven stent along a weave path in the second helical direction; and bending a second loose wire portion of the plurality of wires around the bend point to define a second crown portion, and weaving the second loose wire portion into the body of the pre-woven stent along a weave path in the first helical direction.

In certain embodiments, the method further comprises prior to the bending steps, unweaving the first loose wire portion from the pre-woven stent and unweaving the second loose wire portion from the pre-woven stent, wherein the first and second loose wire portions intersect at a first intersection of the plurality of intersections prior to the unweaving, and the bend point corresponds to the first intersection.

In one approach, the first crown portion and the second crown portion overlap and combine to define a double crown. In certain embodiments, the method further comprises bending further first and second loose wire portions around a further bend point to define further first and second crown portions that overlap and combine to define further double crowns.

In one approach, the end of the first loose wire portion and the end of the second loose wire portion terminate at a point longitudinally inward of a longitudinally outermost intersection of the plurality of intersections. In another approach, the first loose wire portion overlaps an inner wire portion of a wire of the plurality of wires, which wire includes the second loose wire portion, wherein the overlap occurs inboard of the first and second crown portions after the first and second loose wire portions have been woven into the body of the pre-woven stent. In another approach, further weaving of further first and second loose wire portions of the plurality wires defines a double-weave portion of the stent.

In yet another approach, the method further comprises loading the pre-woven stent onto a mandrel having a plurality of cavities having a plurality of posts extending radially outward from the cavities, wherein the plurality of posts extend through the cells of the pre-woven stent. In certain embodiments, the bending of the first loose wire portion includes bending the first loose wire portion around an apex post of the plurality of posts, and the bending of the second loose wire portion includes bending the second loose wire around an apex post of the plurality of posts, wherein the apex post is disposed at the bend point.

In certain embodiments, the method further comprises cutting at least one of the first and second loose wire portions to define a removable tail portion of the at least one of the first and second loose wire portions, and removing the tail portion from the stent. In one approach, the cutting is performed at a cut point located on the first and second crown portion, both the first and second crown portions are cut to define a first and second removable tail portion, and the first removable tail portion includes a bend portion corresponding to the apex of first crown portion and the second tail portion does not include a bend portion corresponding to the second crown portion, further comprising joining the first and second crown portions at the cut point to define a single crown. In another approach, the cutting is performed at a cut point located longitudinally inward of an intersection of the plurality of intersections disposed at a base of the first and second crown portions, and the tail portion includes one of the first and second crown portions, and the other of the first and second crown portions remains in the stent thereby defining a single crown.

In certain embodiments, both of the first and second loose wire portions are cut at the cut point to create a pair of tail portions, one of the tail portions including one of the first and second crown portions and the other tail portion not including either of the first and second crown portions. In one approach, cut ends are defined by cutting both of the first and second loose wire portions, and the cut ends are fixed together. In another approach, only one of the first and second loose wire portions is cut at the cut point and an overlapping portion of the first and second loose wire portions is defined after removing the tail portion.

In another aspect, a medical device in the form of a woven stent includes a body defined by a plurality of wires extending in a first helical direction around the body and extending in a second helical direction around the body, the second helical direction being transverse to the first helical direction. The plurality of wires are woven together to define a plurality of cells and a plurality of intersections. A first crown portion of the stent is disposed at a first end of the stent and defined by a first wire end portion of the plurality of wires, the first crown portion including a bend portion defining an apex of the first crown portion, wherein the wire end portion extends in the first helical direction toward the apex of the crown and bends at the apex of the first crown portion, and further extends and is woven into the stent from the apex of the first crown portion in the second helical direction. A second crown portion of the stent is disposed at the first end of the stent and defined by a second wire end portion of the plurality of wires, the second crown portion including a bend portion defining an apex of the second crown portion, wherein the second wire end portion extends in the second helical direction toward the apex of the second crown portion and bends at the apex of the second crown portion and further extends and is woven into the stent from the apex of the second crown portion in the first helical direction.

In certain embodiments, the first and second crown portions overlap each other to define a double crown. In one approach, the stent includes a plurality of double crown portions extending circumferentially around the first end of the stent.

In another embodiment, the first wire end portion overlaps the second wire end portion to define a double weave portion of the stent. In one approach, the stent includes the double weave portion of the stent including a plurality of double crowns defining the first end of the stent and further includes a single weave portion of the stent including a plurality of crown portions defining a second end of the stent that is opposite the first end. In a further approach, the single weave portion has a larger diameter than the double weave portion. In certain embodiments, the first wire end portion terminates at a wire end disposed longitudinally inward of a longitudinally outermost intersection of the plurality of intersections.

In yet another aspect, a medical device in the form of a woven stent includes a body defined by a plurality of wires extending in a first helical direction around the body and extending in a second helical direction around the body, the second helical direction being transverse to the first helical direction. The plurality of wires are woven together to define a plurality of cells and a plurality of intersections, the plurality of wires define a plurality of wire ends, and the plurality of wire ends are each curved into a rounded looped end to define a first end of the woven stent.

In yet another aspect, a method for manufacturing a stent comprises the steps of: providing a pre-woven stent defining a body having a tubular body portion defined by a plurality of wires extending in a first helical direction around the body and a extending in a second helical direction around the body, the first helical direction being transverse to the second helical direction, wherein the plurality of wires define a plurality of wire ends terminating at a first end plane at a first end of the pre-woven stent, wherein the plurality of wires are woven together to define a mesh; weaving a wire end portion of at least one of the plurality of wires back into the body away from the first end plane and toward a second end that is opposite the first end and defining a crown portion of the wire end portion; wherein the weaving creates an intermediate end plane defined by a bend of the crown portion, the intermediate end plane being spaced away from the first end plane and between the first end plane and the second end; wherein, in response to the weaving steps, the pre-woven stent has a reduced longitudinal length and defines a modified stent having a longitudinal length that is shorter than the pre-woven stent Other devices, systems, methods, features and advantages will be, or will become, apparent to one with skill in the art upon examination of the following figures and detailed description. It is intended that all such additional devices, systems, methods, features and advantages be included within this description, and be protected by the following claims.

BRIEF DESCRIPTION OF THE DRAWINGS

The system may be better understood with reference to the following drawings and description. The components in the figures are not necessarily to scale, with emphasis instead being placed upon illustrating the principles of the present disclosure. Moreover, in the figures, like referenced numerals designate corresponding parts throughout the different views.

DETAILED DESCRIPTION

Definitions

Figure 1:
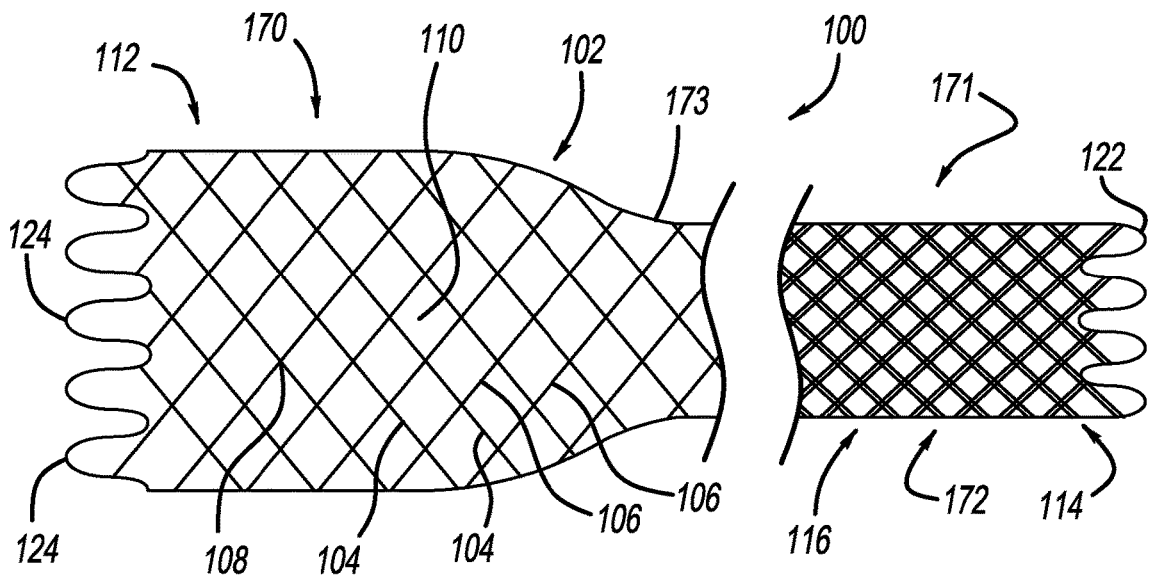
FIG. 1 depicts a side-view of a woven stent including treated ends.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The present disclosure also contemplates other embodiments "comprising," "consisting of" and "consisting essentially of," the embodiments or elements presented herein, whether explicitly set forth or not.

The term "proximal," as used herein, refers to a direction that is generally towards a physician during a medical procedure.

The term "distal," as used herein, refers to a direction that is generally towards a target site within a patient's anatomy during a medical procedure.

The term "biocompatible," as used herein, refers to a material that is substantially non-toxic in the in vivo environment of its intended use, and that is not substantially rejected by the patient's physiological system. A biocompatible structure or material, when introduced into a majority of patients, will not cause an undesirably adverse, long-lived or escalating biological reaction or response. Such a response is distinguished from a mild, transient inflammation which typically accompanies surgery or implantation of foreign objects into a living organism.

Devices and Systems

FIGS. 1-9 depict an embodiment of a woven stent 100. The structure of the stent 100 is formed from a plurality of wires 102 helically wound in an under-over-under configuration. The wires 102 can be defined as a combination of first wires 104 and second wires 106. The first wires 104 extend in a first generally helical direction and the second wires 106 extend in a second generally helical direction.

In one approach, the first and second wires 104, 106 can be separate and distinct wires. In another approach, a pair of the first wires 104 and the second wires 106 can each be portions of a single wire that includes a bend at one end of the stent to define the first wire 104 and second wire 106, with the portion defining the first wire 104 extending in the first helical direction and the portion defining the second wire 106 extending in the second helical direction. For purposes of further discussion, the first and second wires 104, 106 will be described as being separate and distinct wires, unless otherwise noted. But it will be appreciated that the descriptions of these first and second wires 104, 106 can applied to embodiments where pairs of first and second wires 104, 106 are part of one overall bent wire that creates the portions extending in the first and second helical directions.

The first and second helical directions are typically arranged transverse to each other and therefore the first and second wires 104, 106 are likewise arranged transverse to each other. In one approach, the first and second wires 104, 106 are arranged perpendicular to each other at each crosspoint or intersection 108 of the wires 104, 106. However, it will be appreciated that the wires 104, 106 can also be arranged at different transverse angles, such that there are both obtuse and acute angles defined by the wires 104, 106 at the intersection 108.

Cross points in the structure (i.e., where the wire crosses over and under itself) further define a plurality of quadrilateral shaped cells 110 defined at their perimeter by the wires 104, 106. The quadrilateral shape of the cell 110 depends on the orientation of the wires 104, 106 at each of the intersections that define the four corners of the cell 110 as well as the spacing between the wires 104, 106. For example, the quadrilateral shape of the cell 110 could be a square, rectangle, rhombus, parallelogram, or the like. It will be appreciated that the woven nature of the stent 100 will allow for various shapes and sizes of the cells 110 as the stent is radially and/or longitudinally compressed and expanded.

The stent 100 includes a first end portion 112 and a second end portion 114, with a tubular body portion 116 extending longitudinally between the first and second end portion 112, 114. The first and second ends 112, 114 can also be referred to as proximal and distal ends.

The body of the stent 100 is defined by the woven structure of the wires, and the overall body can have different shapes, including an enlarged diameter flange portion at one or both ends. It will be appreciated that reference to the stent body can include reference to portions of the stent that are enlarged to define flange portions, and is not limited to the portion that extends between the flanges, unless otherwise noted. Thus, a reference to wires being woven into the body encompasses wires being woven into the flange portion of a stent having flanges, and also to uniform diameter stents, as well as other distances or portions of the stent.

The stent shown in FIG. 1 has a non-uniform diameter along its length. It will be appreciated that other general tubular shapes, including uniform diameter or multiple portions having different diameters could also be used.

Figure 2:
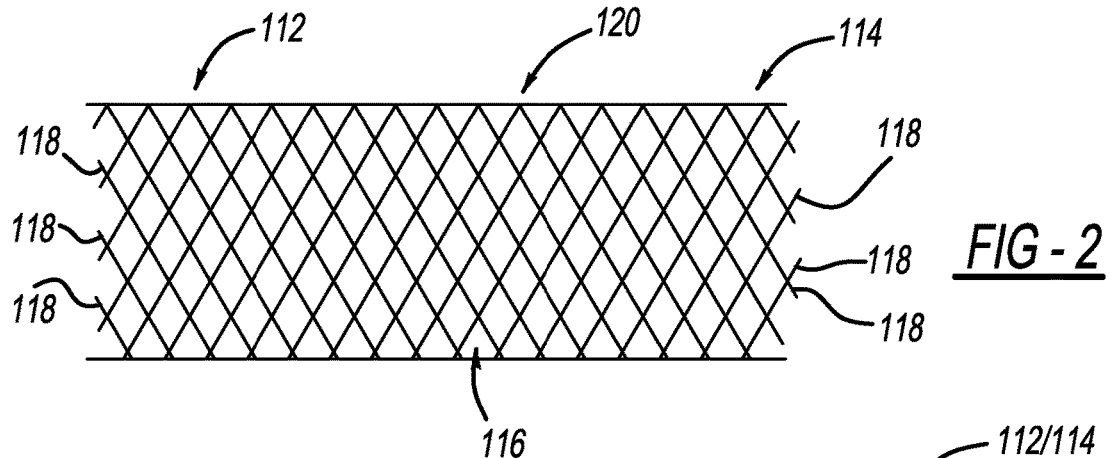
FIG. 2 depicts a side-view of a pre-woven stent.

The stent 100 can be manufactured and woven in a variety of ways known to the art. One method of manufacturing involves the use of a mandrel on which the strands of the stent are overlaid and woven together by hand. Hand weaving of entire stents, however, can be costly as well as time-consuming. Another manner of manufacturing the stent involves machine weaving. Machine woven stents can typically be made quickly and at a reduced cost relative to a hand woven stent. Machine woven stents result in the production of a stent having a plurality of sharp wire ends 118 disposed at each of the first and second end portions or, alternatively, at one end. The resulting machine woven stent can be referred to a pre-woven stent 120, as the pre-woven stent 120 has been woven but still includes the undesirable sharp ends 118 at at least one of the first and second end portions 112, 114. The pre-woven stent 120 is shown in FIG. 2, and is shown having a uniform diameter and with both end having the sharp ends 118 for ease of illustration. It will be appreciated that the pre-woven stent 120 could have just one end having the sharp ends 118, with the opposite end forming bends that link the first and second wires 104, 106, as described above with reference to a single wire having two portions that define the first and second wires 104, 106.

Providing the pre-woven stent 120 having sharp wire ends 118 reduces the time for weaving the stent 100 by providing the user with the majority of the stent 100, including the tubular body portion 116. The pre-woven stent 120, however, includes at least one of the first and second end portion 112, 114 in an unfinished condition having the sharp ends 118. However, these sharp ends 118 can be further modified and treated to ultimately produce the finished version of the stent 100 where the sharp ends 118 are eliminated.

For purposes of discussion, the pre-woven stent 120 will be described as having the sharps ends 118 at both the first and second ends 112, 114. It will be appreciated that references to treating both the first second ends 112, 114 can also apply to treating a single end, with the opposite end not including sharp ends to be treated.

Treating the sharp ends 118 can be accomplished in different ways and can result in different structural characteristics at the first and second end portions 112, 114. In one approach, the first and second ends 112, 114 are modified to include a plurality of crowns 124 (FIG. 1) disposed circumferentially around the first and second end portions 112, 114. In another approach, the first and second ends 112, 114 can be modified to include a plurality of looped ends 125 disposed circumferentially around the first and second end portions 112, 114. The crowns 124 and looped ends 125 will be described in further detail below.

The pre-woven stent 120 can be made either by hand-weaving or machine-weaving. The pre-woven stent 120 includes the plurality of sharp ends 118. The sharp ends 118 are defined by the ends of the wires that are woven together to define the tubular body portion 116. The sharp ends 118 can terminate at approximately the same longitudinal position, or they can terminate at different longitudinal positions. For the purposes of discussion, the sharp ends 118 will be referred to as being at approximately the same longitudinal position.

The pre-woven stent 120 includes the first wires 104 and second wires 106 that extend in transverse helical directions, as described above. The first and second wires 104, 106 are woven together, but typically free to move slightly relative to each other as is typical in a woven structure. Accordingly, each of the wires 104, 106 define the sharp ends 118 at each end. The sharp ends 118 are free ends, and capable of being moved and manipulated, as further described below, to treat the sharp ends 118.

Figure 3:
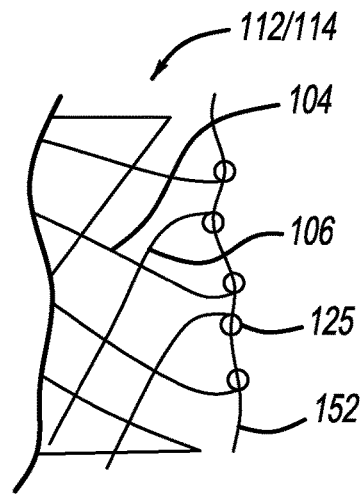
FIG. 3 depicts a partial side-view of an end of the pre-woven stent having been treated by creating looped ends.
Figure 4:
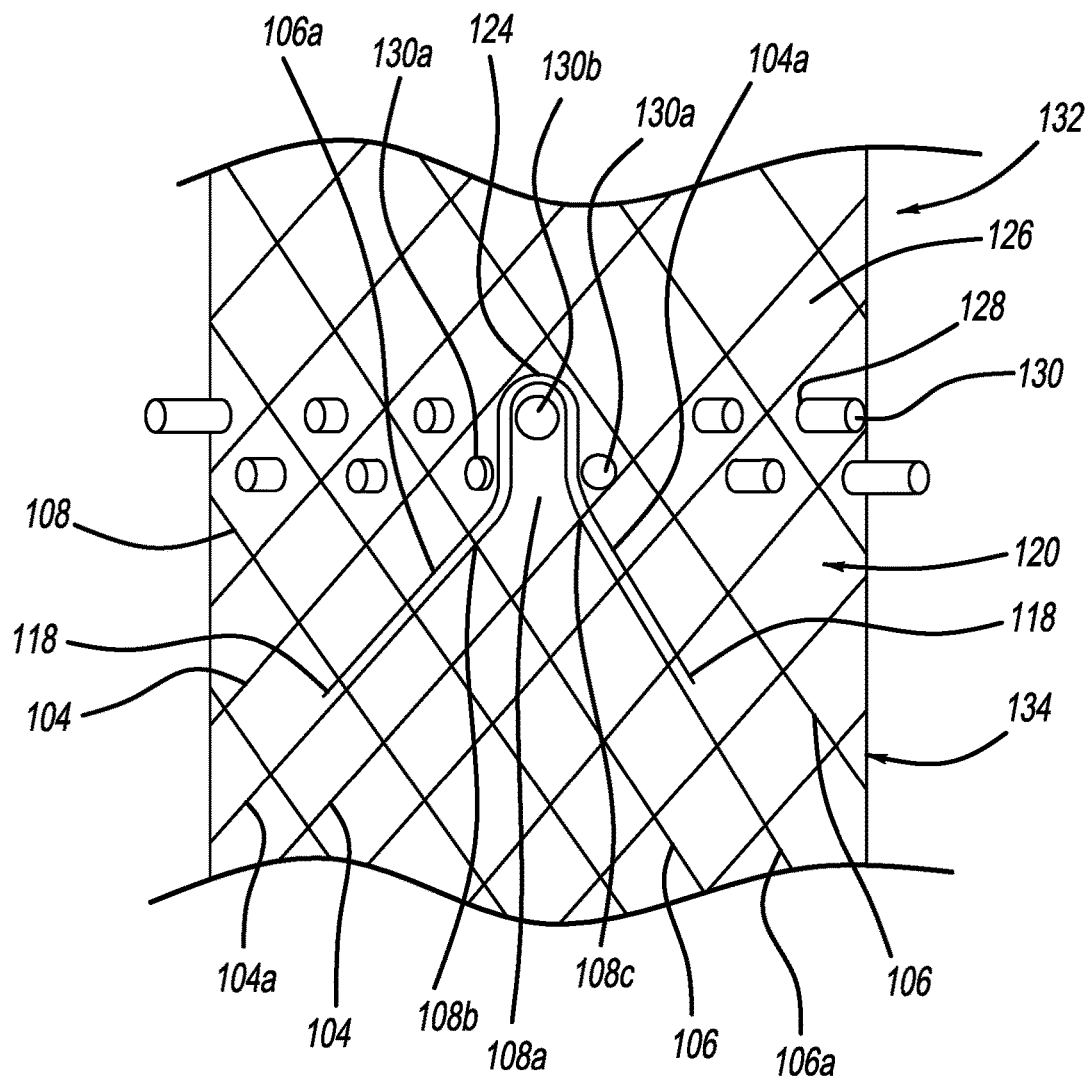
FIG. 4 depicts a side-view of the pre-woven stent being loaded on a mandrel, and a selected pair of wires being unwoven, bent, and re-woven into the stent to create a double-crown.

With reference to FIG. 4, to treat the sharp ends 118, the pre-woven stent 120 having the first and second wires 104, 106 is loaded onto a mandrel 126. The mandrel 126 has a generally cylindrical shape that is sized and configured to be inserted into a lumen defined by the pre-woven stent 120. Preferably, the outer diameter of the mandrel 126 generally corresponds to the inner diameter of the pre-woven stent 120, such that there is only a small amount of radial space between the mandrel 126 and the pre-woven stent 120. However, it will be appreciated that the relative sizes of the mandrel 126 and pre-woven stent 120 can be of different sizes such that a larger radial space is defined therebetween, or even such that there is snug fit between the mandrel 126 and pre-woven stent 120, where the mandrel 126 contacts the inner surface of the pre-woven stent around substantially the entire circumference of the mandrel 126. FIG. 3 illustrates the pre-woven stent overlaid on the mandrel 126.

The relative sizes of the mandrel 126 and pre-woven stent 120 are preferably selected to allow individual ones of the wires 104, 106 of the pre-woven stent 120 to be selectively un-woven and re-woven into the body portion 116 of the stent 100 in the case where the pre-woven stent 120 is modified to define crowns 124 for at least one of the ends of the stent 100. In another approach, individual ones of the wires 104, 106 can be provided in an already un-woven and loose state, where they can be woven into the body portion 116. References to re-weaving herein will be appreciated as also referring to weaving that occurs with wires that were already un-woven or loose when provided.

In the case of modifying the pre-woven stent 120 to define the looped ends 125, the sizes of the mandrel 126 and pre-woven stent 120 do not necessarily need to allow for re-weaving of the wires 104, 106 into the body portion 116 of the stent 100.

The mandrel 126 includes a plurality of recesses or cavities 128 extending radially into the mandrel 126. The cavities 128 are disposed circumferentially around the mandrel 126 and at preferably two different longitudinal locations, such that two adjacent rows of cavities are defined, with the cavities 128 of each row being offset circumferentially relative to each other to define a zig-zag pattern on the mandrel 128.

The cavities 128 are sized and arranged such that posts 130 can be inserted into the cavities 128 of the mandrel 126. The posts 130, once inserted into the mandrel 126, will project radially away from the mandrel 126 and through the cells 110 of the pre-woven stent 120. The posts 130 can be selectively inserted into and removed from the mandrel 126 as desired. The spacing of the cavities 128 around the mandrel 126 is preferably arranged such that a trio of posts 130 can be inserted into adjacent cavities 128 along the zig-zag pattern, with two base posts 130a of the posts 130 being longitudinally aligned and defining the base of a triangle arrangement, and with an apex post 130b of the posts 130 defining the apex of the triangle. The two base posts 130a are preferably arranged such that they will abut adjacent intersections 108 of the pre-woven stent 120.

The intersections 108 where the posts 130 are inserted can be referred to as inner intersections, because these intersections are located at a longitudinal location of the pre-woven stent 120 that is inboard from the ends of the pre-woven stent 120. Accordingly, when the posts are inserted 130, an outer portion 132 and inner portion 134 is defined on opposite sides of the posts 130.

The posts 130 are used for wrapping the wires 104, 106 around the posts 130 to bend the wires 104, 106 and re-weave the wires 104, 106 into the body portion 116 of the stent 100 to define the crowns 124.

Before or after loading the pre-woven stent 120 on the mandrel 126, one of the wires 104 and one of the wires 106 are slipped out of the weave pattern of the pre-woven stent, becoming a first unwoven or loose wire 104a and a second unwoven or loose wire 106a. Put another way, the loose wires 104a, 106a are partially un-woven from the pre-woven stent 129. The loose wires 104a, 106a can also be referred to as wire end portions. The loose wires 104a, 106a can be provided in an un-woven stent such that unweaving them from the pre-woven stent 120 is not necessary. The loose wires 104a, 106a are unwoven over the outer portion 132 but still woven into the pre-woven stent 120 along the inner portion 134. The loose wires 104a, 106a correspond to the wires whose intersection 108a is disposed between the base posts 130a and the apex post 130b when the posts 130 are inserted through the cells 110 of the pre-woven stent 120 and prior to the loose wires 104, 106 being unwoven. In cases where the loose wires 104a, 106a are already un-woven when the pre-woven stent 120 is provided, the apex post 130b is disposed at a location corresponding to the where the loose wires 104a, 106a would have intersected. The intersection 108a is generally disposed within the triangle defined by the base posts 130a and apex post 130b.

The base posts 130a are arranged at an intersection 108b of the first loose wire 104a and one of the second wires 106 that is adjacent and on the inner side of the second loose wire 106a, and at an intersection 108c of the second loose wire 106a and one of the first wires 104 that is adjacent and on the inner side of the first loose wire 104a. The base posts 130a are on the outer side of the intersections 108b and 108c.

With the loose wires 104a and 106a being free from the pre-woven stent 120, either after being provided in that state of after being un-woven from the pre-woven stent 120, they are then re-woven into the pre-woven stent 120 to begin defining the stent 100. The first loose wire 104a is bent around the adjacent base post 130a at an obtuse angle toward the apex post 130b. The first loose wire 104a is bent and wrapped around the apex post 130b at an acute angle and back toward the opposite base post 130a. The first loose wire 104a is then bent around the base post 130a, where it is subsequently woven back into the body portion 116 of the stent 100. The first loose wire 104a is woven along the path of the second loose wire 106b within the inner portion 134. The bending around the apex post 130b of the first wire 104a defines at least a portion of the crown 124. Put another way, the first loose wire 104a is bent and extends from its bend in the second helical direction and overlaps a body portion of the wire that includes the second loose wire 106a.

The second loose wire 106a is bent around the posts 130a and 130b in a similar manner, but from the opposite side. The second loose wire 106a is bent along substantially the same path as the first loose wire 104a was bent. The second loose wire 106a is woven back into the stent 100 within the inner portion 134 along the path of the first loose wire 104a. The second loose wire 106a thereby defines another portion of the crown 124.

Accordingly, the first and second loose wires 104a and 106a overlap each other along the crown 124, and also along the path of the wires that include the first and second loose wires 104a, 106a on the inner side of the posts 130. With the first and second loose wires 104a, 106a forming the crown 124 and being re-woven into the stent 100, the outer portion 134 of the pre-woven stent 120 therefore has fewer wires remaining.

In another approach, the mandrel 126 can include a plurality of recessed tracks, or the like, that extend in the first and second helical directions corresponding to the weave pattern of the stent. The tracks can also bend one or more ends corresponding to the shape of the desired crown, such that the bend point of the crown is defined by the track. This approach can be used as an alternative to the posts 130 for controlling the shape of the bend.

As described, the crown 124 is in the form of a double crown 124, such that the first loose wire 104a (or the wire end portion of the first wire 104 that is bent) defines a first crown portion and the second loose wire 106a (or the wire end portion of the second wire 106 that is bent) defines a second crown portion. Formation of a first double crown 124 is shown in FIG. 4.

Reference to the loose wires 104a, 106a refers to the wire end portions that are un-woven or provided in an un-woven condition. It will be appreciated that once the loose wires 104a, 106a are re-woven into the stent, they are no longer "loose," and that reference to the loose wires 104a, 106a after being re-woven refers to these portions even though they are no longer "loose."

The process of slipping the wires 104, 106 out of the outer portion 134 of the pre-woven stent 120 and being re-woven into the stent 100 can be repeated for further pairs of the first and second wires 104, 106 if necessary. To repeat the process, the posts 130 can be removed and inserted into adjacent cavities 128. Alternatively, the mandrel 126 can have posts 130 inserted into each of the cavities 128, thereby not requiring removal and re-insertion of the posts 130 in the desired cavities 128. After repeating the process for additional selected pairs of wires 104, 106, a corresponding number of additional double crowns 124 will be defined for each pair of wires 104, 106, with double crowns 124 disposed around the entire circumference of the stent 100.

The process can be repeated at the opposite end of the pre-woven stent 120, if desired. The stent 100 can be removed from the mandrel and reloaded on the mandrel to treat the untreated end, or the mandrel can include cavities 128 and posts 130 for both ends such that removal and reloading of the stent 100 on the mandrel is no necessary. In some instances, as described previously, the pre-woven stent 120 will include an end that does not include sharp ends 118 and therefore would not be reloaded to treat that end.

Figure 5:
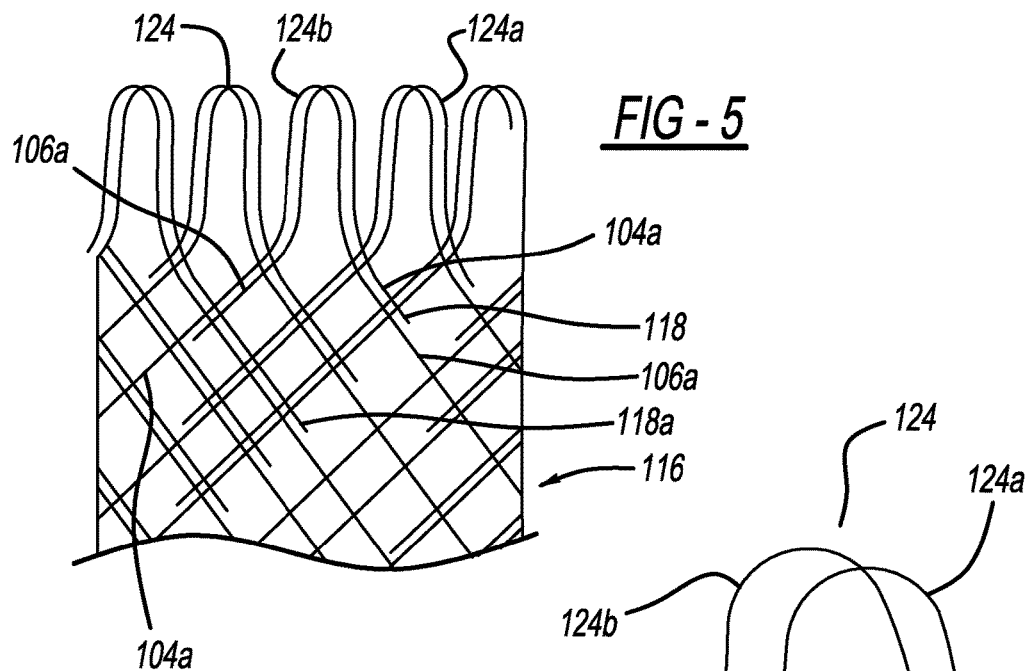
FIG. 5 depicts a side-view of a stent having double crowns.

As shown in FIG. 4, when the wires 104, 106 are re-woven into the stent, the sharp ends 118 are no longer free ends, and they terminate within the body portion of the stent 100. With reference to FIG. 5, the point of termination or end 118a of the wires 104, 106 can be disposed at different longitudinal locations along the body portion 116 of the stent 100. The ends 118a of the wires 104a, 106a after being re-woven into the stent 100 can be left as free ends (not fixed), as their disposal within the body of the stent 100 limits instances of the ends of the wires 104a, 106a puncturing tissue when the stent 100 is deployed. Alternatively, the ends 118a of the wires 104a, 106a can be welded, bonded, soldered, glued, or otherwise adhered to the portion of the wire 104a, 106a along which they extend. The ends 118a of the wires 104a, 106a could also be attached by attached a tungsten marker band around the end of the wires 104a, 106a. In another approach, the stent 100 can be coated with a silicone membrane, resulting in an encapsulation of the ends 118a of the wires 104, 106.

The amount of the wires 104, 106 that extend back into the stent 100 and overlap with other wires 104, 106 will result in the stent 100 having a portion of the body portion 116 in the form of a double weave, as shown in FIG. 5. The wires 104, 106 can extend deep into the body, or can extend a short distance into the body, depending on the amount of extension desired for the double weave portion of the body portion 116. FIG. 1 illustrates a double weave portion that extends a large distance into the body portion 116, which is further described below.

After the process of the re-weaving each of the wires 104, 106 is complete, the resulting stent 100 is free from the sharp ends 118, and the ends 118a are instead disposed within the body portion 116. Instead, at least one of the end portions 112, 114 of the stent 100 include a plurality of crowns 124 disposed circumferentially around the end or ends of the stent 100.

The process described above defines the crowns 124 as double crowns, meaning that each of the wires 104, 106 defines a crown portion 124a and 124b, respectively. The crown portions 124a, 124b combine to define the crown 124 in the form of a double crown.

The above described method of weaving the wires 104, 106 into the body of the stent 100 has been described such that the wire 104, 106 are paired together, where the wire 104 overlaps the wire 106, and vice versa. In another approach, the wire 104 can be bent and weaved into the body of the stent 100 along a path that is offset from the wire 106, but still extending in the same helical direction as the wire 106. Put another way, instead of the wires 104 and 106 overlapping each other when bent and weaved back into the stent, the wire 104 would overlap a wire adjacent the wire 106 (or even a wire further offset from the wire 106), and the wire 106 would overlap a wire adjacent the wire 104 (or even a wire further offset from the wire 104. In this approach, the crown portions 124a and 124b would not overlap to define a double crown, but would instead be circumferentially staggered relative to each other.

In an alternative approach, the wires 104, 106 can be cut or otherwise terminated to result in a crown in the form of a single crown 140. The single crown 140 can be created in various ways, as further described below. Formation of the single crown 140 generally involves cutting the wires 104, 106 and removing a tail portion of one or more of the wires 104, 106 such that it does not overlap the other of the wires 104, 106 in the area of the single crown 140. Single crowns can also be provided as part of the pre-woven stent 120 at the end opposite the sharp ends 118, when the pre-woven stent only includes the sharp ends 118 at one end. In this case, these pre-woven single crowns are not created by treating the sharp ends 118, as they are already provided with the pre-woven stent 120.

Figure 6:
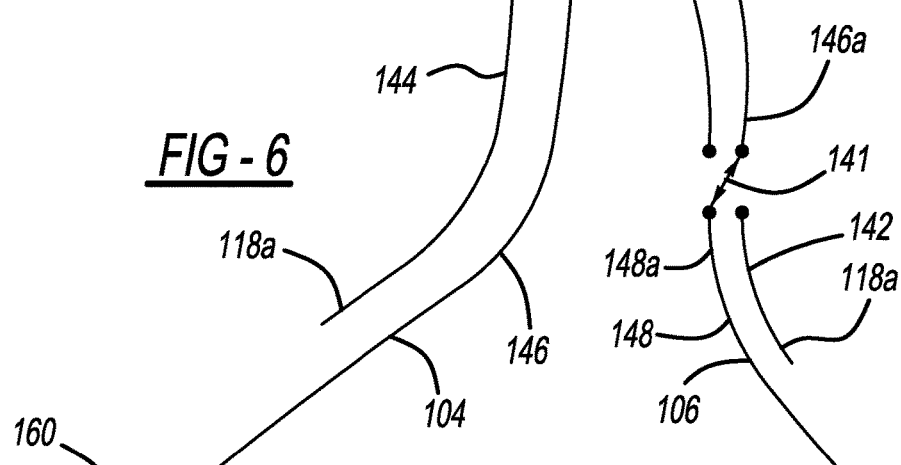
FIG. 6 depicts a double crown being cut for being converted to a single crown.
Figure 7:
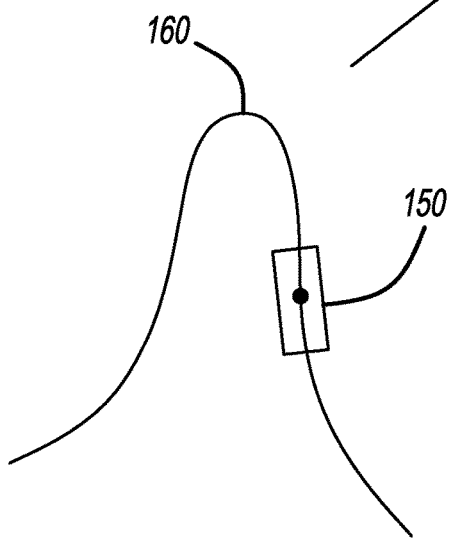
FIG. 7 depicts a single crown created from FIG. 6.

In one approach, as illustrated in FIGS. 6 and 7, after creating the double crown 124, the double crown 124 is cut at a point 141 on the side of the crown 124, inboard of the apex of the crown 124. The cut point 141 can be disposed on either side of the apex, and between the apex and one of the intersections 108a corresponding to the crown 124 being cut. Upon cutting the crown 124, a first tail portion 142 of one of the crown portions 124a, 124b is created, with the first tail portion 142 being removable from the stent 100. Additionally, a second tail portion 144 is created from the other of the crown portions 124a, 124b, the second tail portion 144 being removable from the stent 100. The first tail portion 142 does not include the apex of the crown 124, while the second tail portion 144 includes the apex of the crown 124. Each of the first and second tail portions 142, 146 includes the end 118a of the wires 104, 106 that was woven back into the stent 100.

After removing both of the first and second tail portions 142, 144, body portions 146 and 148 of the wires 104, 106 remain woven into the stent 100. The body portions 146, 148 include ends 146a, 148a, respectively, that terminated generally at the location of the cut point 141. The ends 146a, 148a can thereafter be joined together to create the single crown 140, as shown in FIG. 7. In this case, there is no overlapping portion between wires 104, 106, as their respective ends terminate at the point of their joining. The ends 146a, 146b can be joined with a sleeve 150, or tungsten marker band, or other crimping mechanism. In another approach, a stainless steel cannula can be used to join the ends 146a, 148a. Other methods of joining the ends 146a, 148a include, but are not limited to, a heat shrink sleeve, soldering, welding, brazing, bonding, gluing, membrane coating, tying, or the like.

Figure 8:
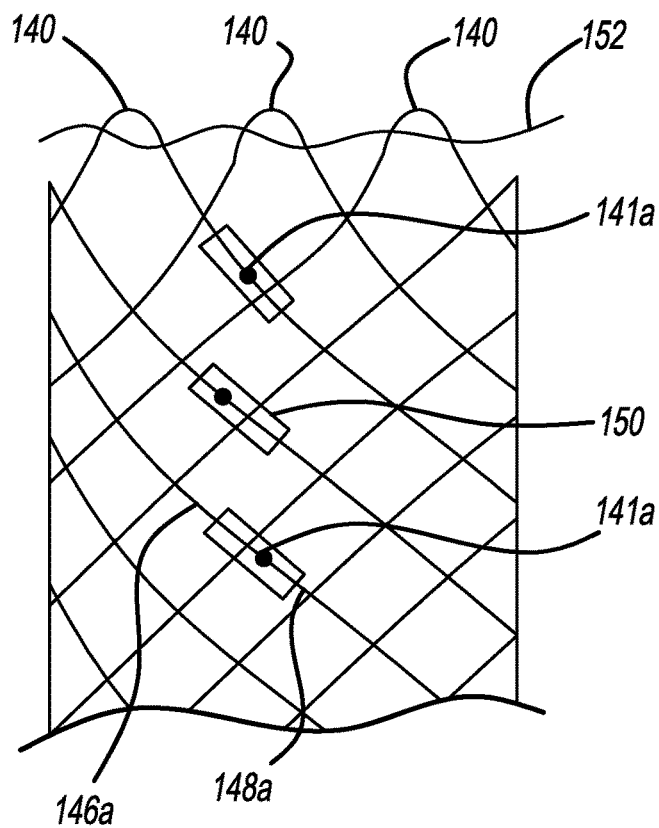
FIG. 8 depicts a side view of a stent having single crowns after a pair of wires were cut at points longitudinally inward from the crowns.

With reference to FIG. 8, in an alternative approach, the cut point 141 can be made at a location inboard of the crown 124, such that a cut point 141a is used. Moreover, the cut point 141a for each crown 124 can be at different longitudinal locations for each crown 124. Thus, the cut points 141a and joining of the body portions 146a, 148a can be longitudinally aligned rather than being circumferentially aligned.

Figure 9:
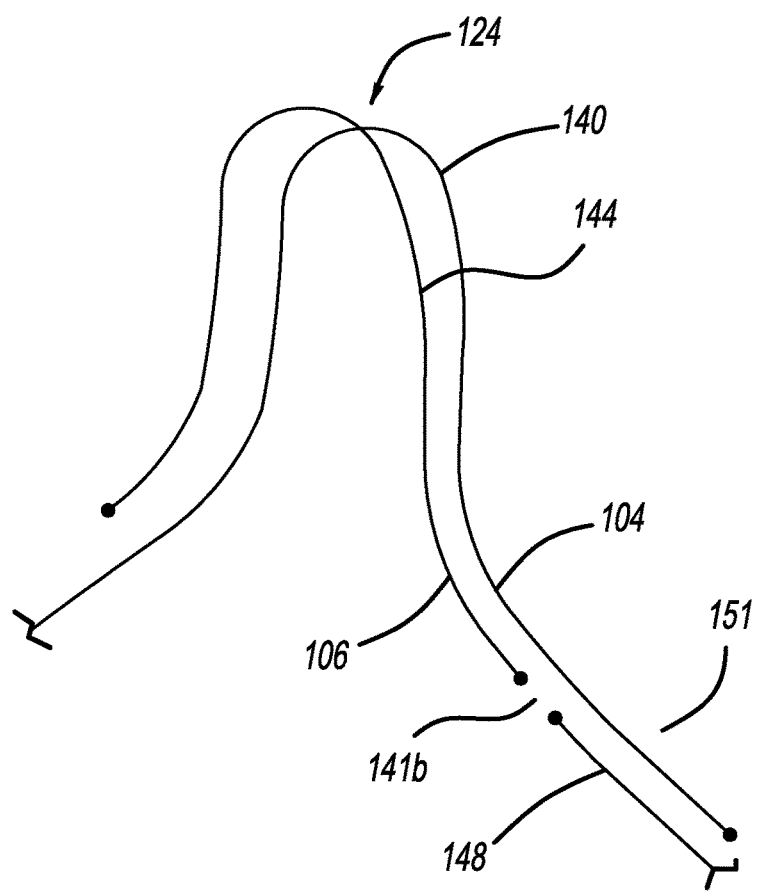
FIG. 9 depicts a single crown being formed by cutting a single wire of a pair of wires that form a double crown to remove one crown portion of the double crown.

In another approach, as shown in FIG. 9, only one of the wires 104, 106 can be cut at a cut point 141b. Cutting one of the wires 104, 106 creates a single tail portion 144 that can be removed from the stent 100 and a single body portion 148 that remains part of the stent 100. The single tail portion 144 includes the apex of the crown portion 124a or 124b that is removed from the crown 124, thereby creating the single crown 140. In this approach, by cutting only one of the wires 104, 106 and removing the single tail portion 144, there remains an overlapping portion 151 between wires 104 and 106, with the body portion 148 overlapping the wire 104/106 that was not cut. The wires of the overlapping portion 151 can be joined in a manner previously described, such as bonding, welding, encapsulation via sleeve or membrane, or the like. Alternatively, the overlapping portion 151 can be free from being joined. Additionally, cutting of a single wire can be performed at the location of the wire end 118a, such that there is no overlapping portion.

In the approaches using cut points 141a or 141b, the resulting single crown 140 is formed by one wire 104/106 whose entire crown portion 124a/124b remains (FIGS. 8 and 9). In the approach using cut point 141, the resulting single crown 140 is formed by two wires 104, 106 joined together (FIGS. 6 and 7).

The above described approaches to treating one or more ends of the pre-woven stent 120 to remove the sharp ends 118 and create the stent 100 have been accomplished by creating crowns 124 or 140. The crowns 124, 140 can be joined together via a suture 152 (see FIG. 8) looped or woven through the crowns 124, 140, where the suture 152 can be used to control the expansion of the stent 100 in a manner known in the art.

It will be appreciated that above described double crown 124 or single crown 140 can be used together in the same stent 100, with one end of the stent 100 having double crowns 124 and the other end of the stent 100 having single crowns. Alternatively, one or both ends of the stent 100 can include both double crowns 124 and single crowns 140, either in an alternating circumferential fashion, or with double crowns 124 in one circumferential portion and single crowns 140 in another circumferential portion, or at non-uniform locations circumferentially around the ends of the stent 100.

In another approach, and with reference back to FIG. 3, rather than creating crowns at the ends of the stent 100, the sharp ends 118 of the wires 104, 106 can be treated by looping the ends of each individual wire independent from the others. In this approach, the sharp ends 118 are curled or bent in a tight spiral to define the looped end 125, the looped end 125 defining an opening therethrough. The looped ends 160 of the stent can be coupled to each other via the suture 152 described above to collapse the ends of the stent 100 and control deployment in a manner known in the art. The looped ends 125 can define one or both ends of the stent 100.

The above described stent 100 has been described as having a tubular body portion 116. The tubular body portion 116 can have a uniform diameter or different diameters, and include a wide flange portion 170 in addition to a narrow body portion 171, where the flange portion 170 has a larger diameter than the body portion 171, as illustrated in FIG. 1. The flange portion 170 is typically used for being disposed in the healthy area of a patient's tissue, and the presence of the flange portion 171 in that area helps ensure that the stent 100 does not migrate to other portions of the body lumen in which the stent 100 is disposed. However, if the tips of the crowns 124, 140 push too hard on the patient's healthy tissue, this can cause discomfort. Accordingly, it can be desirable to reduce the radial force in the flange portion 170 and the crown section of the flange portion 170.

The above described methods of re-weaving the wires 104, 106 can be used to reduce the radial force in the flange portion 170 relative to the narrow body portion 171. As described above, the wires 104, 106 can be re-woven into the stent body portion to create a double weave portion 172. In this approach, the double weave can extend substantially along the narrow body portion 171, with the double weave ending at a transition section 173 between the narrow body portion 171 and the flange portion 170.

In one approach, the flange portion 170 includes a single weave arrangement with single crowns 140 or looped ends 160. The diameter of the wires 104, 106 is selected such that, when used as a double weave, gives approximately the same radial force as the thickness of a wire used in a single weave stent for the particular application of the stent 100. For example, if a traditional stent is normally woven with a 0.008 inch NiTi wire, then the stent 100 can be made with a 0.004 inch NiTi wire (or whatever dimension would result in the same radial force when double woven as the single 0.008 inch wire). It will be appreciated that the thickness of the wire in the stent 100 will not necessarily be half of the size of the wire used in a traditional single weave stent. For example, a 0.003 inch wire when doubled may result in the same radial force when double woven as a 0.008 wire, or a 0.005 inch wire when doubled may result in the same radial force when double woven as a 0.008 inch wire.

Accordingly, by double weaving the narrow body portion 171 and single weaving the flange portion 170, the narrow body portion 171 will have an increased radial force relative to the flange portion 170, and the flange portion 170 will therefore have a reduced radial force relative to the narrow body portion 171.

In another approach, both the narrow body portion 171 and the flange portion 170 can include a double weave, while still resulting in reduced radial force at the crowns 124/140 of the stent 100. This is due to the double crowns 124 having portions 124a and 124b that are not woven together, but rather able to shift and bend relative to each other. While it may be expected that the double crown 124 has a harder or stiffer feel, this is not the case when they can move relative to each other. On the contrary, the double crowns 124 have a softer more compliant feel to them relative to a single crown formed of a thicker wire, and a similar compliant feel as a single crown 140 formed of the same wire thickness. Thus, when using the double crowns 124 or single crowns 140 described in the present application, the body portion 171 and/or flange portion 170 being double woven will have increased radial force similar to a single woven stent of a greater thickness, the crowns 124 themselves do not exhibit the same increase in radial force, and are therefore more compliant than the double woven body portion 171, thereby increasing patient comfort and/or reducing patient discomfort.

The above described disclosure of the stent 100 and methods of treating the sharp ends 118 of a pre-woven stent 120 provides an inexpensive and consistent stent production of the pre-woven stent 120 while allowing for the sharp ends 118 to be treated to reduce patient discomfort. The various terminated ends of the wires 104, 106 of the above embodiments are not subject to the same stress concentrations at weld or bond joints of prior methods of treating the ends of pre-woven stents. Reasons for the lower stress concentration include that the crown portions are free from welding or bonding in some instances, or that welding or bonding that does occur can be limited to joining only two wires in some instances, where prior methods joined more than two wires and therefore receive increased loading at such a joint.

A stent according to the present disclosure may have any suitable braid angle. The radial force of the stent may be controlled by adjusting the braid angle accordingly. Stents with higher braid angles typically exert greater radial force and exhibit greater foreshortening during expansion from a compressed state. Stents with lower braid angles typically exert lower radial force and experience less foreshortening upon expansion. In some instances, if the stent is partially or fully covered with a membrane material, the braid angle can be lowered because membrane coverings typically add rigidity to the stent structure. In addition to adjusting the braid angle, the radial force of the stent can be adjusted through selection of particular materials as well as the shape and size of the filaments or wires forming the stent structure.

Although the illustrated embodiments depict a stent having a central body portion and a flange, other stent configurations are possible. For example, a stent may include a double flange, two asymmetrically shaped flanges, or may entirely lack flanges and instead have a uniform or substantially uniform diameter along the entire length of the stent. A stent may include a uniform diameter along the length of the stent but include slightly flared proximal and/or distal ends. The central body portion may smoothly transition to a flange or flare, or alternatively, may progressively step up in diameter to a flange or flare. Generally, a stent may be implanted in a vessel (e.g., esophagus, duodenum, colon, trachea, or the like) such that the central body portion engages a diseased area and the flanges or ends engage healthy tissue adjacent the diseased area. Preferably, the flanges are configured to anchor the stent at the site of implantation, thereby reducing the incidence of proximal and distal migration. Preferably, the flanges are sized and shaped to accommodate the vessel or organ of implantation. For example, stents destined for lower esophageal implantation may have differently shaped and sized flanges compared to a stent designed for upper esophageal implantation. In addition to the soft crowns, the flanges may include other features or configurations designed to reduce incidence of tissue perforation and overgrowth. For example, the ends (e.g., the crown cells) of the flanges may curve or bend inward toward the stent lumen to minimize tissue damage at or near the stent ends. In certain embodiments, a stent may include other design elements configured to secure the stent at the site of implantation. For example, in certain embodiments, a stent may include small anchors, clips, hooks, or barbs that will anchor the stent to the internal wall of the targeted body lumen. In other embodiments, the stent may be sutured to the site of implantation at one or more portions of the stent structure.

A stent including treated ends may include one or more components configured to aid in visualization and/or adjustment of the stent during implantation, repositioning, or retrieval. For example, a stent may include one or more radiopaque markers configured to provide for fluoroscopic visualization for accurate deployment and positioning. Radiopaque markers may be affixed (e.g., by welding, gluing, suturing, or the like) at or near the ends of the stent at a cross point of filament(s) in the braid pattern. In certain embodiments, a stent may include four radiopaque markers with two markers affixed to a first flange and two to a second flange. Optionally, radiopacity can be added to a stent through coating processes such as sputtering, plating, or co-drawing gold or similar heavy metals onto the stent. Radiopacity can also be included by alloy addition. Radiopaque materials and markers may be comprised of any suitable biocompatible materials, such as tungsten, tantalum, molybdenum, platinum, gold, zirconium oxide, barium salt, bismuth salt, hafnium, and/or bismuth subcarbonate.

A stent including treated ends may include one or more loops, lassos, or sutures on the stent structure to facilitate repositioning or removal of the stent during or after implantation. For example, a stent may include a loop at or near the proximal end of the stent. The loop material may circumscribe the flange and in certain embodiments may be wound through the absolute end cells to affix the loop to the stent. The loop may comprise any appropriate biocompatible material, such as for example, suture materials or other polymeric or metallic materials such as polyethylene, ultra-high molecular weight polyethylene, polyester, nylon, stainless steel, nitinol, or the like. Optionally, the lasso may be coated with a material, such as polytetrafluoroethylene, to reduce frictional interactions of the lasso with surrounding tissue.

Stents including treated ends may be self-expanding, mechanically expandable, or a combination thereof. Self-expanding stents may be self-expanding under their inherent resilience or may be heat activated wherein the stent self-expands upon reaching a predetermined temperature or range of temperatures. One advantage of self-expanding stents is that traumas from external sources or natural changes in the shape of a body lumen do not permanently deform the stent. Thus, self-expanding stents may be preferred for use in vessels that are subject to changes in shape and/or changes in position, such as those of the peripheral and gastrointestinal systems. Peripheral vessels regularly change shape as the vessels experience trauma from external sources (e.g., impacts to arms, legs, etc.); and many gastrointestinal vessels naturally change shape as peristaltic motion advances food through the digestive tract. One common procedure for implanting a self-expanding stent involves a two-step process. First, if necessary, the diseased vessel may be dilated with a balloon or other device. The stent may be loaded within a sheath that retains the stent in a compressed state for delivery to the targeted vessel. The stent may then be guided to the target anatomy via a delivery catheter and thereafter released by retracting or removing the retaining sheath. Once released from the sheath, the stent may radially expand until it contacts and presses against the vessel wall. In some procedures, self-expanding stents may be delivered with the assistance of an endoscope and/or a fluoroscope. An endoscope provides visualization as well as working channels through which devices and instruments may be delivered to the site of implantation. A fluoroscope also provides visualization of the patient anatomy to aid in placement of an implantable device, particularly in the gastrointestinal system.

Mechanically expandable stents (e.g., balloon expandable stents) having treated ends may be made from plastically deformable materials (e.g., 316L stainless steel). A balloon-expandable stent may be crimped and delivered in a reduced diameter and thereafter expanded to a precise expanded diameter. Balloon expandable stents can be used to treat stenosed coronary arteries, among other vessels. One common procedure for implanting a balloon expandable stent involves mounting the stent circumferentially on a balloon-tipped catheter and threading the catheter through a vessel passageway to the target area. Once the balloon is positioned at the targeted area, the balloon may be inflated to dilate the vessel and radially expand the stent. The balloon may then be deflated and removed from the passageway.

Expandable stents according to the present disclosure may be formed by any suitable method as is known in the art. In certain embodiments, the expandable stents may be fabricated by braiding, weaving, knitting, crocheting, welding, suturing, or otherwise machining together one or more filaments or wires into a tubular frame. Such stents may be referred to as braided, woven, or mesh stents. A braided stent may be fabricated by, for example, use of a braiding mandrel having specifically designed features (e.g., grooves and detents) for creating such a stent. A variety of braiding patterns are possible, such as for example, one-under and one-over patterns or two-under and two-over patterns. The filaments or wires may be of various cross-sectional shapes. For example, the filaments or wires may be flat in shape or may have a circular-shaped cross-section. The filaments or wires may have any suitable diameter, such as for example, from about 0.10 to about 0.30 mm. As will be described in greater detail below, the expandable stents may formed from a variety of biocompatible materials. For example, the filaments or wires may comprise one or more elastically deformable materials such as shape memory alloys (e.g., 304 stainless steel, nitinol, and the like).

A stent including treated ends may be made from any suitable biocompatible material(s). For example, a stent may include materials such as stainless steel, nitinol, MP35N, gold, tantalum, platinum or platinum iridium, niobium, tungsten, iconel, ceramic, nickel, titanium, stainless steel/titanium composite, cobalt, chromium, cobalt/chromium alloys, magnesium, aluminum, or other biocompatible metals and or composites or alloys. Examples of other materials that may be used to form stents include carbon or carbon fiber; cellulose acetate, cellulose nitrate, silicone, polyethylene terephthalate, polyurethane, polyamide, polyester, polyorthoester, polyanhydride, polyether sulfone, polycarbonate, polypropylene, ultra high molecular weight polyethylene, polytetrafluoroethylene, or another biocompatible polymeric material, or mixtures or copolymers of these; polylactic acid, polyglycolic acid or copolymers thereof; a polyanhydride, polycaprolactone, polyhydroxybutyrate valerate or another biodegradable polymer, or mixtures or copolymers of these; a protein, an extracellular matrix component, collagen, fibrin, or another biologic agent; or a suitable mixture of any of these.

A stent including treated ends may be fabricated to any suitable dimensions. A stent having a particular length and diameter may be selected based on the targeted vessel. For example, a stent designed for esophageal implantation may have a length ranging from about 5 cm to about 15 cm and a body diameter of about 15 mm to about 25 mm. Optionally, an esophageal stent may include one or more flanges or flares of about 10 mm to about 25 mm in length and about 20 mm to about 30 mm in diameter. A stent designed for colon implantation may have a length ranging from about 5 cm to about 15 cm and a body diameter of about 20 mm to about 25 mm. Optionally, a colonic stent may include one or more flanges having a diameter of about 25 mm to about 35 mm.

In certain embodiments a stent with treated ends may include a membrane covering over the stent framework. A stent may include covering over the entire stent framework from the proximal end to the distal end. Alternatively, the stent may have covering over a central portion of the structure but have uncovered ends or flanges. Where the stent flanges include a membrane covering, preferably the soft crowns lack membrane covering between other adjacent crowns so that the crowns may move independently from one another. Any suitable biocompatible material may be used as the membrane covering. Preferably, the membrane covering is an elastic or flexible material that can adapt to radial compression of a stent prior to delivery, as well as foreshortening of a stent during expansion from a compressed state. Suitable membrane materials include, for example, silicones (e.g. polysiloxanes and substituted polysiloxanes), polyurethanes, thermoplastic elastomers, polyolefin elastomers, polyethylene, polytetrafluoroethylene, nylon, and combinations thereof. In one preferred embodiment, the membrane covering comprises silicone. In certain embodiments, where the stent will be implanted at or near an acidic environment (e.g., will be exposed to gastric fluids), preferably the membrane covering is resistant to acid degradation.

The membrane covering may be applied to a stent by any suitable method as is known in the art. For example, the membrane may be applied by spraying, dipping, painting, brushing, or padding. Generally, the membrane covering or coating has a thickness ranging from about 0.0025 mm to about 2.5 mm, from about 0.01 mm to about 0.5 mm, or from about 0.03 mm to about 0.07 mm. The thickness of the membrane may be selected, for example, by controlling the number of dips or passes made during the application process. In one exemplary embodiment, a braided stent may be dipped in silicone liquid, removed, and thereafter cured. Preferably, the coating extends over the abluminal and luminal surfaces of the filaments, and also resides in the cells or interstices defined by the filament braid pattern.

In certain embodiments, a stent with treated ends may include one or more bioactive agents coated on the stent surfaces. A bioactive agent may be applied directly on the surface of the stent (or on a primer layer which is placed directly on the surface of the stent). Alternatively, the bioactive agent may be mixed with a carrier material and this mixture applied to the stent. In such configuration, the release of the bioactive agent may be dependent on factors including composition, structure and thickness of the carrier material. The carrier material may contain pre-existing channels, through which the bioactive agent may diffuse, or channels created by the release of bioactive agent, or another soluble substance, from the carrier material.

One or more barrier layers may be deposited over the layer containing the bioactive agent. A combination of one or more layers of bioactive agent, mixtures of carrier material/bioactive, and barrier layers may be present. The bioactive agent may be mixed with a carrier material and coated onto the stent and then over coated with barrier layer(s). Multiple layers of bioactive agent, or mixtures of carrier material/bioactive, separated by barrier layers may be present to form a multicoated stent. Different bioactive agents may be present in the different layers.

The carrier material and/or the barrier layer can include a bioelastomer, PLGA, PLA, PEG, Zein, or a hydrogel. In certain other embodiments, the carrier material and/or the barrier layer includes microcrystalline cellulose, hydroxypropylmethyl cellulose, hydroxypropyl cellulose, a cellulose product, a cellulose derivative, a polysaccharide or a polysaccharide derivative. The carrier material and/or barrier layer may include lactose, dextrose, mannitol, a derivative of lactose, dextrose, mannitol, starch or a starch derivative. The carrier material and/or barrier layer may include a biostable or a biodegradable material, for example, a biostable or biodegradable polymer.

A variety of bioactive agents may be applied to the stent in accordance with the intended use. For example, bioactive agents that may be applied include antiproliferative/antimitotic agents including natural products such as vinca alkaloids (vinblastine, vincristine, and vinorelbine), paclitaxel, rapamycin analogs, epipodophyllotoxins (etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (for example, L-asparaginase which systemically metabolizes L-asparagine and deprives cells which do not have the capacity to synthesize their own asparagine); antiplatelet agents such as (GP) II b/IIIa inhibitors and vitronectin receptor antagonists; antiproliferative/ antimitotic al kylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives (cyclosporine, tacrolimus (FK-506), sirolimus (rapamycin), tacrolimus, everolimus, azathioprine, mycophenolate mofetil); angiogenic agents: vascular endothelial growth factor (VEGF), fibroblast growth factor (FGF); angiotensin receptor blockers; nitric oxide and nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; endothelial progenitor cells (EPC); angiopeptin; pimecrolimus; angiopeptin; HMG co-enzyme reductase inhibitors (statins); metalloproteinase inhibitors (batimastat); protease inhibitors; antibodies, such as EPC cell marker targets, CD34, CD133, and AC 133/CD133; Liposomal Biphosphate Compounds (BPs), Chlodronate, Alendronate, Oxygen Free Radical scavengers such as Tempamine and PEA/NO preserver compounds, and an inhibitor of matrix metalloproteinases, MMPI, such as Batimastat.

A bioactive agent may be applied, for example, by spraying, dipping, pouring, pumping, brushing, wiping, vacuum deposition, vapor deposition, plasma deposition, electrostatic deposition, ultrasonic deposition, epitaxial growth, electrochemical deposition or any other method known to the skilled artisan.

Prior to applying a membrane, and/or a bioactive agent, a stent may be polished, cleaned, and/or primed as is known in the art. A stent may be polished, for example, with an abrasive or by electropolishing. A stent may be cleaned by inserting the stent into various solvents, degreasers and cleansers to remove any debris, residues, or unwanted materials from the stent surfaces. Optionally, a primer coating may be applied to the stent prior to application of a membrane covering, bioactive, or other coating. Preferably, the primer coating is dried to eliminate or remove any volatile components. Excess liquid may be blown off prior to drying the primer coating, which may be done at room temperature or at elevated temperatures under dry nitrogen or other suitable environments including an environment of reduced pressure. A primer layer may comprise, for example, silane, acrylate polymer/copolymer, acrylate carboxyl and/or hydroxyl copolymer, polyvinylpyrrolidone/vinylacetate copolymer (PVP/VA), olefin acrylic acid copolymer, ethylene acrylic acid copolymer, epoxy polymer, polyethylene glycol, polyethylene oxide, polyvinylpyridine copolymers, polyamide polymers/copolymers polyimide polymers/copolymers, ethylene vinylacetate copolymer and/or polyether sulfones.

A stent according to the present disclosure may be delivered to a body lumen using various techniques. Generally, under the aid of endoscopic and/or fluoroscopic visualization a delivery device containing the stent is advanced into the vicinity of the target anatomy. The targeted lumen may be predilated with a balloon catheter or other dilation device, if necessary. Preferably, the stent is delivered in a compressed state in a low profile delivery device. This approach may reduce the risk of tissue perforations during delivery. Once the delivery device is in place, the stent may be released from the retaining sheath or the like. In one preferred embodiment, a stent may be delivered with a controlled release system (e.g., Evolution™ Controlled-Release Stent, Cook Endoscopy Inc., Winston-Salem, N.C.). A controlled release device permits the physician to slowly release the stent from the retaining sheath and in some instances, recapture the stent to allow for repositioning. After implantation, the delivery device and any other devices (e.g., wire guides, catheters, etc.) may be removed.

While various embodiments of the presently disclosure have been described, it will be apparent to those of ordinary skill in the art that many more embodiments and implementations are possible within the scope of the present disclosure. Accordingly, the disclosure is not to be restricted except in light of the attached claims and their equivalents.

The invention claimed is:

1. A method for treating one or more ends of a pre-woven stent to manufacture a stent, the method comprising the steps of:
    providing a pre-woven stent defining a body having a tubular body portion, a first end portion, and a second end portion defined by a plurality of wires extending in a first helical direction around the body and extending in a second helical direction around the body, the first helical direction being transverse to the second helical direction, wherein the plurality of wires define a plurality of wire ends terminating at the first end portion, wherein the plurality of wires are woven together to define a plurality of cells and a plurality of intersections;
    bending a first loose wire portion of the plurality of wires around a bend point to define a first crown portion, and weaving the first loose wire portion into the body of the pre-woven stent along a weave path in the second helical direction; and
    bending a second loose wire portion of the plurality of wires around the bend point to define a second crown portion, and weaving the second loose wire portion into the body of the pre-woven stent along a weave path in the first helical direction.

2. The method of claim 1 further comprising, prior to the bending steps, unweaving the first loose wire portion from the pre-woven stent and unweaving the second loose wire portion from the pre-woven stent, wherein the first and second loose wire portions intersect at a first intersection of the plurality of intersections prior to the unweaving, and the bend point corresponds to the first intersection.

3. The method of claim 1, wherein the first crown portion and the second crown portion overlap and combine to define a double crown.

4. The method of claim 3, further comprising bending further first and second loose wire portions around a further bend point to define further first and second crown portions that overlap and combine to define further double crowns.

5. The method of claim 1, wherein the end of the first loose wire portion and the end of the second loose wire portion terminate at a point longitudinally inward of a longitudinally outermost intersection of the plurality of intersections.

6. The method of claim 1, wherein the first loose wire portion overlaps an inner wire portion of a wire of the plurality of wires, which wire includes the second loose wire portion, wherein the overlap occurs inboard of the first and second crown portions after the first and second loose wire portions have been woven into the body of the pre-woven stent.

7. The method of claim 1, wherein further weaving of further first and second loose wire portions of the plurality of wires defines a double-weave portion of the stent.

8. The method of claim 1, further comprising loading the pre-woven stent onto a mandrel having a plurality of cavities having a plurality of posts extending radially outward from the cavities, wherein the plurality of posts extend through the cells of the pre-woven stent.

9. The method of claim 8, wherein the bending of the first loose wire portion includes bending the first loose wire portion around an apex post of the plurality of posts, and the bending of the second loose wire portion includes bending the second loose wire around the apex post of the plurality of posts, wherein the apex post is disposed at the bend point.

10. The method of claim 1, further comprising cutting at least one of the first and second loose wire portions to define a removable tail portion of the at least one of the first and second loose wire portions, and removing the tail portion from the stent.

11. The method of claim 10, wherein the cutting is performed at a cut point located on the first and second crown portion, both the first and second crown portions are cut to define a first and second removable tail portion, and the first removable tail portion includes a bend portion corresponding to the apex of first crown portion and the second tail portion does not include a bend portion corresponding to the second crown portion, further comprising joining the first and second crown portions at the cut point to define a single crown.

12. The method of claim 10, wherein the cutting is performed at a cut point located longitudinally inward of an intersection of the plurality of intersections disposed at a base of the first and second crown portions, and the tail portion includes one of the first and second crown portions, and the other of the first and second crown portions remains in the stent thereby defining a single crown.

13. The method of claim 12, wherein both of the first and second loose wire portions are cut at the cut point to create a pair of tail portions, one of the tail portions including one of the first and second crown portions and the other tail portion not including either of the first and second crown portions.

14. The method of claim 13, wherein cut ends are defined by cutting both of the first and second loose wire portions, and the cut ends are fixed together.

15. The method of claim 12, wherein only one of the first and second loose wire portions is cut at the cut point and an overlapping portion of the first and second loose wire portions is defined after removing the tail portion.

* * * * *